(12) United States Patent
Mohamed et al.

(10) Patent No.: US 9,579,520 B2
(45) Date of Patent: Feb. 28, 2017

(54) METHOD OF ORTHOPEDIC TREATMENT BY RADIATION

(71) Applicants: Hossam Abdel Salam El Sayed Mohamed, Ottawa (CA); Houda Abdul Rahman M. AL Mansour, Ottawa (CA)

(72) Inventors: Hossam Abdel Salam El Sayed Mohamed, Ottawa (CA); Houda Abdul Rahman M. AL Mansour, Ottawa (CA)

( * ) Notice: Subject to any disclaimer, the term of this patent is extended or adjusted under 35 U.S.C. 154(b) by 0 days.

(21) Appl. No.: 14/861,067

(22) Filed: Sep. 22, 2015

(65) Prior Publication Data

US 2016/0008626 A1 Jan. 14, 2016

Related U.S. Application Data

(62) Division of application No. 13/919,361, filed on Jun. 17, 2013, now abandoned.

(51) Int. Cl.
*A61N 5/06* (2006.01)
*A61N 5/067* (2006.01)

(52) U.S. Cl.
CPC ........... *A61N 5/0601* (2013.01); *A61N 5/0613* (2013.01); *A61N 2005/066* (2013.01);
(Continued)

(58) Field of Classification Search
CPC ................ A61N 5/0601; A61N 5/0613; A61N 2005/066; A61N 2005/067; A61N 2005/0612; A61N 2005/0659; A61B 2018/00464
See application file for complete search history.

(56) References Cited

U.S. PATENT DOCUMENTS 4,564,011 A 1/1986 Goldman
4,872,458 A * 10/1989 Kanehira ............. A61B 18/082
600/104
(Continued)

FOREIGN PATENT DOCUMENTS

EP 2449994 A1 9/2012

OTHER PUBLICATIONS

Misbah H. Khan, Frank Victor, Babar Rao, Neil S. Sadick, Treatment of cellulite: Part II. Advances and controversies, Journal of the American Academy of Dermatology, vol. 62, Issue 3, Mar. 2010, pp. 373-384.*

(Continued)

*Primary Examiner* — Lynsey Crandall
*Assistant Examiner* — Nathan J Jenness
(74) *Attorney, Agent, or Firm* — Caesar Rivise, PC (57) ABSTRACT

An orthopedic infra-red laser medical device and methods of use for applying infra-red energy to an anatomic region of interest located within the body of a patient. The device includes a hollow needle and a housing on which the needle is releasably mounted. The housing includes an infra-red laser source for producing a laser beam and directing the beam through the needle to exit out of the open distal end of the needle. The distal end of the needle is sharp to pierce through the skin of the patient to a position closely adjacent the anatomic region of interest to deliver the infra-red laser beam thereto without any intervening skin and tissue attenuating the infra-red laser beam. The device can be used for various orthopedic purposes and can also be used on fat in a patient to release activated stem cells.

3 Claims, 7 Drawing Sheets

(52) U.S. Cl.
CPC ...... *A61N 2005/067* (2013.01); *A61N 2005/0612* (2013.01); *A61N 2005/0659* (2013.01)

(56) References Cited

U.S. PATENT DOCUMENTS

| | | | |
|---|---|---|---|
| 5,954,710 A * | 9/1999 | Paolini | A61B 18/22 606/15 |
| 6,200,332 B1 | 3/2001 | Del Giglio | |
| 6,371,954 B1 | 4/2002 | Lee | |
| 2004/0224288 A1 | 11/2004 | Bornstein | |
| 2004/0260367 A1 | 12/2004 | De Taboada et al. | |
| 2007/0219540 A1 | 9/2007 | Masotti et al. | |
| 2012/0289859 A9 | 11/2012 | Nicoson et al. | |

OTHER PUBLICATIONS

Kujawa, J., et al., Low-Intensity near-infrared laser radiation-induced changes of acetylcholinesterase activity of human erythrocytes. J Clin Laser Med Surg Dec. 2003;21(6):351-5, Abstract.

Jolanta Kujawa, et al., Effect of Low-Intensity (3.75-25 J/cm2) Near-Infrared (810 nm) Laser Radiation on Red Blood Cell ATPase Activities and Membrane Structure, Journal of Clinical Laser Medicine & Surgery, Apr. 2004, 22(2): 111-117. doi:10.1089/104454704774076163, Abstract.

Javad T. Hashmi, MD, et al., Effect of Pulsing in Low-Level Light Therapy, NIH Public Access, Author Manuscript, Lasers Surg Med. Aug. 2010 ; 42(6): 450-466. doi:10.1002/lsm.20950.

Paul A. Lapchak, Transcranial near-infrared laser therapy applied to promote clinical recovery in acute and chronic neurodegenerative diseases, NIH Public Access, Author Manuscript, Expert Rev Med Devices. Jan. 2012 ; 9(1): 71-83. doi.10.1586/erd.11.64.

Levon Gasparyan, et al., Influence of Low Level Laser Radiation on Migration of Stem Cells, Laser Florence 2004, pp. 1-7.

Dr. Roberta T. Chow, et al., Efficacy of low-level laser therapy in the management of neck pain: a systematic review and meta-analysis of randomised placebo or active-treatment controlled trials, The Lancet, vol. 374, No. 9705, p. 1897-1908, Dec. 5, 2009, DOI: http://dx.doi.org/10.1016/S0140-6736(09)61522-1.

Seyed Mansoor Rayegani MD, et al., Low Intensity Laser Therapy, Basics and clinical applications, Journal of Lasers in Medical Sciences, vol. 1, No. 1, Autumn 2010, pp. 31-34.

D. Simanovskii, et al., Cellular tolerance to pulsed heating, SPIE Proceedings, Laser-Tissue Interactions XVI, vol. 5695, BIOS 2005, pp. 1-6.

Ying-Ying Huang, Biphasic Dose Response in Low Level Light Therapy, Dose Response 2009; 7(4) 358-383, Published online Sep. 1, 2009. doi: 10.2203/dose-response.09-027.Hemblin, pp. 1-17, http://www.ncbi.nlm.nih.gov/pmc/articles/PMC2790317/.

International Search Report for PCT/IB2013/001316 mailed Dec. 2, 2013.

* cited by examiner

Fig. 13

METHOD OF ORTHOPEDIC TREATMENT BY RADIATION

CROSS-REFERENCE TO RELATED APPLICATIONS

This divisional application claims the benefit under 35 U.S.C. §121 of application Ser. No. 13/919,361 filed on Jun. 17, 2013 entitled Orthopedic Infra-red Laser Medical Device and Methods of Use. The entire disclosure of this application is incorporated by reference herein.

FIELD OF THE INVENTION

This invention relates generally to medical devices and methods of use and more particularly to infra-red (IR) laser devices and methods of use for treating orthopedic diseases and conditions.

BACKGROUND OF THE INVENTION

It is well established that Infra-red has many benefits to the human body and there are many clinics that use infra-red for treatment of aging process and its related complications. The problem is that infra-red cannot penetrate deep tissues. Thus, historically its main use for therapeutic purposes has been directed to skin and the very near subcutaneous tissues Recently, the introduction of pulsed infra-red laser that can penetrate deeper tissues for approximately three inches has enabled the treatment of chronic pain. Moreover, some centres in the United States and Canada have claimed that pulsed infra-red laser treatment can successfully replace some surgical interventions in many painful and refractory diseases. Although this new advanced technique helps many patients, the skin still consumes about 50% of the beam energy so that tissues and structures deeper than three inches cannot get good benefit from the Pulsed IF therapy.

Thus, a need exists to provide infra-red radiation to deeper tissues/structures, e.g., the back of lumbar discs or a midfemur fracture, with good concentration for viable therapeutic results and without damaging the skin, i.e., exceeding what is called the skin tolerance limit.

The subject invention addresses those needs.

The patent literature includes disclosures of some infra-red devices for treating some medical conditions by delivering the infra-red radiation through a cannula into the body of a patient. Examples of such prior art devices are shown in U.S. Published Patent App. Nos. 2012/0289859 (Nicoson et al.) and in European Patent App. No. EP 2 449 994.

SUMMARY OF THE INVENTION

In accordance with one aspect of the invention there is provided an infra-red laser device for applying infra-red energy to an anatomic region of interest located within the body of a patient. The device basically comprises a housing and a needle. The needle is an elongated member having a proximal end, a sharpened distal end and a hollow passageway extending therethrough from the proximal end to the distal end. The housing comprising an infra-red laser source located therein. The infra-red laser source is arranged when activated to produce a collimated infra-red laser beam. The needle is secured to the housing, whereupon the infra-red laser beam produced by the infra-red laser source when activated enters into the hollow passageway at the proximal end of the needle and passes therethrough to exit the distal end of the needle. The distal end of the needle is arranged to pierce through the skin of the patient to a position closely adjacent the anatomic region of interest to directly deliver the infra-red laser beam thereto without any intervening skin and tissue attenuating the infra-red laser beam.

In accordance with one aspect of the invention the Near Infra-red (NIF) laser beam is a continuous beam in the range of approximately 0.7 μm to 3.0 μm.

In accordance with another aspect of the invention the Far Infra-red (FIF) laser beam in a continuous beam in the range of approximately 50 μm to 1000 μm.

Another aspect of this invention entails methods of treating an orthopedic disease or condition of a patient by the irradiation of an anatomic region of interest located within the body of the patient. Such methods basically entail providing a device like described above and introducing the needle of that device into the body of the patient, whereupon the distal end of the needle is located closely adjacent the situs of the anatomic region of interest. The laser source can then be activated to produce the collimated infra-red laser beam, whereupon the infra-red laser beam exits the distal end of the needle to impinge the anatomic region of interest without the intervening skin and underlying tissue attenuating the infra-red laser beam.

The methods of this invention can be used to treat any of the following orthopedic diseases or conditions: osteomyelitis, avascular necrosis, supraspinatus tendinitis, Patelofemoral maltracking, low back pain, delayed healing of a bone fracture, carpal tunnel syndrome, Planter fasciitis, Osteo-arthritis, and Coccydynia.

DETAILED DESCRIPTION OF THE PREFERRED EMBODIMENT

Figure 1:
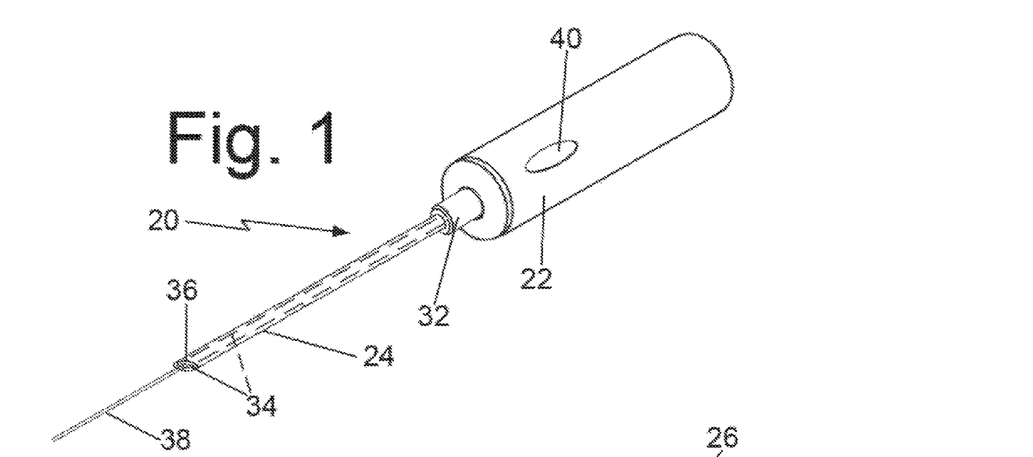
FIG. 1 is an isometric view of one exemplary infra-red laser device, e.g., a hand-holdable device, constructed in accordance with this invention for producing an infra-red laser beam to carry out the various methods of this invention in patients.

Referring now to the various figures of the drawing wherein like reference characters refer to like parts, there is shown in FIG. 1 at 20 an infra-red laser device constructed in accordance with one exemplary embodiment of this invention and which can be used for carrying any of the methods of this invention. With respect to those methods, it must be pointed out that this application describes various exemplary orthopedic diseases or conditions that the subject invention is directed to. Those diseases or conditions are only exemplary. Thus, other infra-red laser devices and methods of use are also contemplated and deemed covered by the subject invention.

Before describing the details of the device 20 and methods of this invention a brief summary of the infra-red technology insofar as its clinic effect is in order. To that end, as is known, there are three basic types of infra-red radiation, namely: Far Infra-red (FIR), Mid infra-red (MIR), and Near infra-red (NIR). FIR ranges in wavelength from approximately 50 μm to approximately 1000 μm. It stimulates Mesenchymal cells (MSCs). Such stem cells can regenerate tissues. Recent studies published indicate that active MSCs can help in re-setting the human body system to its default baseline. This is basis for stem cells injection. MIR ranges in wavelength from approximately 3 μm to approximately 50 μm. MIR apparently has no any clinical significance. NIR has a wavelength in range of approximately 0.7 μm to approximately 3 and constitutes the shortest wave length of infra-red radiation. NIR can be absorbed by pigmented structures of human bodies including hemoglobin, chromosomes of the nucleus, and cytochrome oxidase enzymes of the mitochondria.

Infra-red radiation has several benefits at the cellular or molecular level. For example, FIR facilitates new bone formation. In particular, FIR stimulates RUNX2 (a transcription factor for MSCs of bone marrow which leads to new bone formation). Such activity is very important for elderly person because many of them suffer from osteoporosis and concomitant reduction of bone mass, thereby rendering them more susceptible to fracture with mild trauma. Pulsed FIR delivered from outside the body has also been used for reducing fat in the abdomen and for harvesting abdominal fat (which is rich in MSCs) so that it can be re-injected into the patient's face to reduce wrinkles by the action of MSCs in regenerating facial tissue.

It is believed that the release and activation of MSCs from deeper lying abdominal fat by the application of infra-red radiation thereto offers the possibility causing the activated MSCs to circulate in the blood stream for deposit in every organ of human body, thereby allowing regeneration of every organ of human body with subsequent loss of large part of abdominal fat. It is well known that abdominal fat exerts a marked stress on the joints of spine, the pelvis and lower limbs accelerating their degenerative changes. Therefore, reduction of abdominal fat indirectly reduces degenerative changes of the joints.

However, as noted above, the main drawback of such action is the skin barrier that consumes 50% of the applied IR energy. Thus, to be effective in the IR dosage applied from an external IR laser source would have to be significantly greater, which could damage the intervening skin. The subject invention overcomes this drawback via by-passing the skin, subcutaneous, and muscles barriers.

NIR laser radiation is absorbed by pigmented structures, e.g., hemoglobin, chromosomes of the nucleus, and cytochrome oxidase enzyme of inner membrane of the mitochondria. This results in various benefits of NIR. One benefit is as an anti-oxidant. In particular, externally applied NIR laser radiation is absorbed by cytochrome oxidase which is responsible for energy production by the mitochondria in the form of ATPs particles. As is known, ATPs are the chemical structures of stored energy inside human cells. This action will reduce the pathway for energy production via Kerb's cycle (the cycle of oxidation of food to obtain energy with production of many free radicals). Free radicals are believed to be the most important factor in acceleration of the aging process by oxidative damaging the vital structures of human proteins. Therefore, NIR reduces the production of free radicals so it is indirectly considered as antioxidants. NIR also tends to increase protein synthesis. In particular, NIR is absorbed by the chromosomes which are present as double helix DNA. Recent studies show that NIR causes double helix DNA to be in unwound position and this will facilitate new protein synthesis because translation of proteins needs double helix DNA to be in an unwound state. This also saves energy needed at the cellular level for unwinding the double helix DNA.

Externally applied NIR is successfully used in treatment of chronic arthritis, tendinitis, synovitis, bursitis, etc. The mechanism of action for treatment of chronic pain by NIR is by local increase of blood supply, which accelerates the healing process and removes the mediators responsible for pain by washing them out to blood stream. Activation of nearby dormant MSCs may also serve to repair the damaged tissues by the mechanism similar to stem cells injection. The increased blood supply may also increase immune cells to clean tissue debris, which delays healing process and break down later to form pain mediators.

NIR is absorbed by hemoglobin inside red blood cells (RBCs). No mitochondria are found in RBCs so the energy necessary for their maintenance is obtained only by glycolysis (anaerobic oxidation of glucose with lactic acid production). Recent studies show that NIR has energy that could be utilized by RBCs for their maintenance, especially for cell membrane vitality via the sodium/potassium pump mechanism. Since RBCs are responsible for carrying oxygen from the lungs to tissues then carrying carbon dioxide from tissues back to the lung their increased vitality should enhance local peripheral tissue oxygenation.

It should be pointed out at this juncture that practically speaking all IR lasers are not pure NIR or FIR. Rather, they are typically of mixed wavelengths, with different percentages of the mixture. Therefore, all the above benefits of FIR and NIR are present together and they are called the molecular benefits of infra-red because they happen inside the cells.

Infra-red laser therapy both (FIR and NIR) have the problem that about 50% are lost in the skin barrier. Even the remaining 50% gradually become weaker and weaker while they are travelling away from the skin until they become completely lost.

Figure 2:
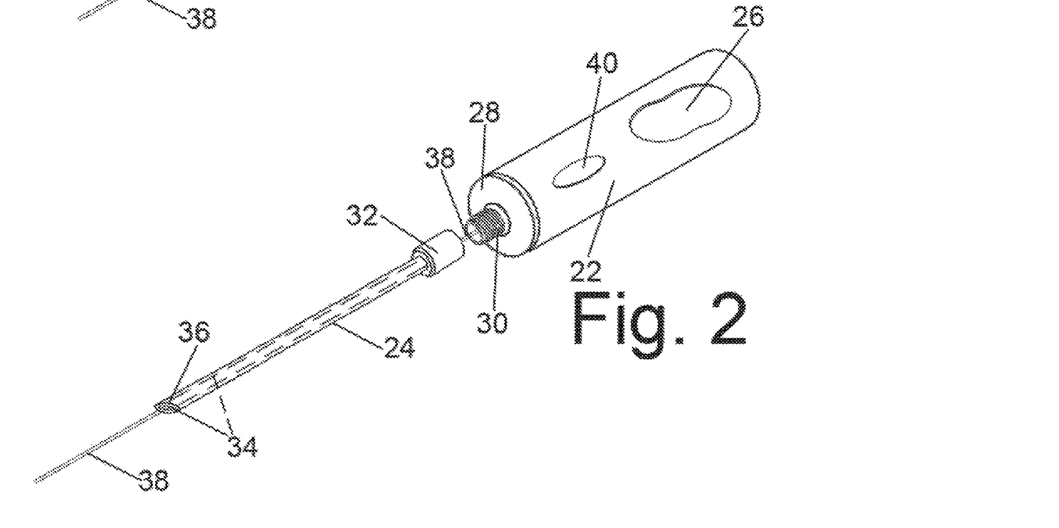
FIG. 2 is an exploded isometric view, partially in section, of the exemplary infra-red laser device shown in FIG. 1.

Turning now to FIG. 1 it can be seen that the device 20 basically comprises a housing 22 and a needle 24. The housing is a hollow member in which an IR laser source 26 (FIG. 2) of any conventional construction is located. The housing is of any suitable shape and size to enable it to be readily held in the hand of a physician or other health care provider. In the exemplary embodiment it is of cylindrical shape and has a distal end wall 28 including an externally threaded, hollow connector 30 (FIG. 2). The connector 30 is arranged to be releasably secured to a connector forming a portion of the needle 24 to mount the needle on the housing. In particular, the needle 24 is an elongated hollow linear member having an enlarged hollow hub or connector 32 at its proximal end. The connector 32 is internally threaded to mate with the external threads of the connector 30 of the housing 22. A passageway 34 of circular cross-section extends from the hollow interior of the connector 32 to the distal end 36 of the needle. The distal end 36 of the needle is open and is sharpened, e.g., cut or beveled an acute angle. Thus, the entire length of the passageway 34 from the proximal end of the needle to the open distal end is unobstructed. The IR source 26 is arranged to produce a collimated IR laser beam 38 at an outlet port (not shown) located within the housing 22 at the proximal end thereof and disposed immediately adjacent the hollow interior of the threaded connector 30. An ON/OFF switch or button 40 is located on the housing 22 and coupled to the laser source 26. The laser source 26 is arranged to be activated to produce the IR laser beam 38 upon depressing or moving the button 40 to the ON position. Accordingly, when the needle 24 is mounted on the housing and the IR laser beam 38 is produced the IR laser beam exits the sharpened distal end 36 of the needle.

The needle 24 is arranged to be manipulated by manipulating the housing so that the needle pierces the skin and underlying anatomic tissue/structures of a patient to bring the open distal end 36 of the needle to a position closely adjacent some deep tissue/structure which forms the region to be irradiated by the IR laser beam (hereinafter called the "region of interest"). Thus, a clear and unobstructed passageway from the laser source to the region of interest results for the laser beam to traverse un-attenuated by the intervening skin, subcutaneous tissue, muscle and any other anatomic tissue/structure(s).

In accordance with one preferred exemplary embodiment of this invention the needle 24 is relatively long, e.g., 3 to 4 inches and of a large gauge (wide bore caliber), such as 14 G or wider, depending upon the disease/condition to be treated and the location of the region of interest. The sharpened or beveled tip 36 of the needle facilitates its passage through the skin and intervening anatomic tissue/structures to the region of interest. If desired, smaller caliber needles may also be used with a medical device constructed in accordance with the subject invention. Such an alternative device may make use of a laser source capable of producing a smaller caliber beam, e.g., a Nano-laser. With such smaller caliber laser instruments, the process of may be carried out without the need for anesthesia, since a smaller caliber needle is less traumatic.

Use of the IR laser device 20 to bring the un-attenuated IR laser beam to the region of interest, e.g., the deep tissue/structure, is accomplished in a similar manner to the injection of fluids into the body of a patient via a conventional needle or syringe. To that end, the device 20 is used by first scraping the skin of the patient with an antiseptic solution, as in case of injection by ordinary fluid-injecting syringe. It is preferable to apply a topical skin anaesthetic for those use applications wherein the needle 24 is of a particularly large gauge or wide bore caliber needle to avoid patient discomfort. The hub or connector 32 of the appropriate sized needle 24 is then threadedly engaged onto the connector 30 at the distal end of the housing, so that the port of the laser source from which the IR laser beam 38 emanates is in communication with the proximally located entry to the hollow interior or passageway 34 extending through the needle. Once the needle is secured to the housing, its sharpened distal end 36 can be brought into engagement with the skin of the patient overlying the region of interest to be irradiated with the laser beam, e.g., the diseased situs. The device 20 can then be pushed forward to introduce the needle through the skin, and the underlying tissue/anatomic structure(s) so that the sharpened free distal end of the needle is closely adjacent the region of interest. The ON/OFF button 40 on the device can then be depressed to cause the laser source 24 to produce the IR laser beam 38. That beam passes through the passageway 34 of the needle and out of the open distal end so that the exiting beam is at full potency where it exits and is un-attenuated by the intervening skin, subcutaneous and muscle barriers. Moreover, being a collimated beam, the exiting IR laser can be focused onto the region of interest to irradiate the tissue/structure at that region. That beam will be reflected and scattered as a result of its impingement on the tissue/structure at the region of interest to a produce what can be called an IR diffusion zone. The IR diffusion zone is shown schematically by the multiple dots designated by the reference number 42 (FIGS. 3-13). The laser device 20 can be manipulated to move the distal end of the needle to any desired position to increase and/or shape the distraction zone to spread the IR radiation throughout the whole region of interest. For example, as will be described later, in case of treating arthritis in the knee joint, the needle can be inserted in the knee joint and then manipulated to spread the IR laser radiation to most of articular cartilage.

Turning now to FIGS. 3-13 there are shown various uses of a laser device 20, like that disclosed above. It should be pointed out that the other types of IR laser devices, than the exemplary embodiment shown in FIG. 1, can be used for the various methods, providing that whatever laser device is used, it makes use of a needle arranged to pierce through the skin and underlying tissue/structures to a position closely adjacent the region of interest to bring an un-attenuated IR laser beam thereto. Thus, the subject invention enables the treatment of deep seated structures, which heretofore were able to receive only a very little percentage of externally applied pulsed IF laser radiation because 50% of the laser beam was lost in the skin barrier and the remaining 50% gradually lost as the beam passes from the skin to the underlying tissue to a maximum of approximately three inches at which virtually all of the energy is lost. In contradistinction, with the subject invention's ability to deliver an un-attenuated IR laser beam to deep seated tissue/structure, five common advantages are achieved and repeated with IR utilization in every disease process. Those five common advantages are as follows. The local heat produced by the IR laser beam should increase the local blood supply with increased tissue oxygenation of ischemic deep structure, thereby reversing the disease process. Moreover, the increased blood supply should have a washing effect in removing of mediators responsible for pain. The laser beam should effectuate the local increase of immune cells to clean up of tissue debris (devitalized tissues) that otherwise impede the healing process. The laser beam should also stimulate dormant MSCs and effect the unwinding of double helix DNA, thereby increasing protein synthesis to accelerate the healing process. All of those five common effects are repeated in every disease process with some variations according to the depth of situs, the severity of the disease process, the blood supply of area surrounding the site of interest. The foregoing five common effects of the IR laser will be discussed with each disease process for which the subject invention has utility.

Figures 3, 4:
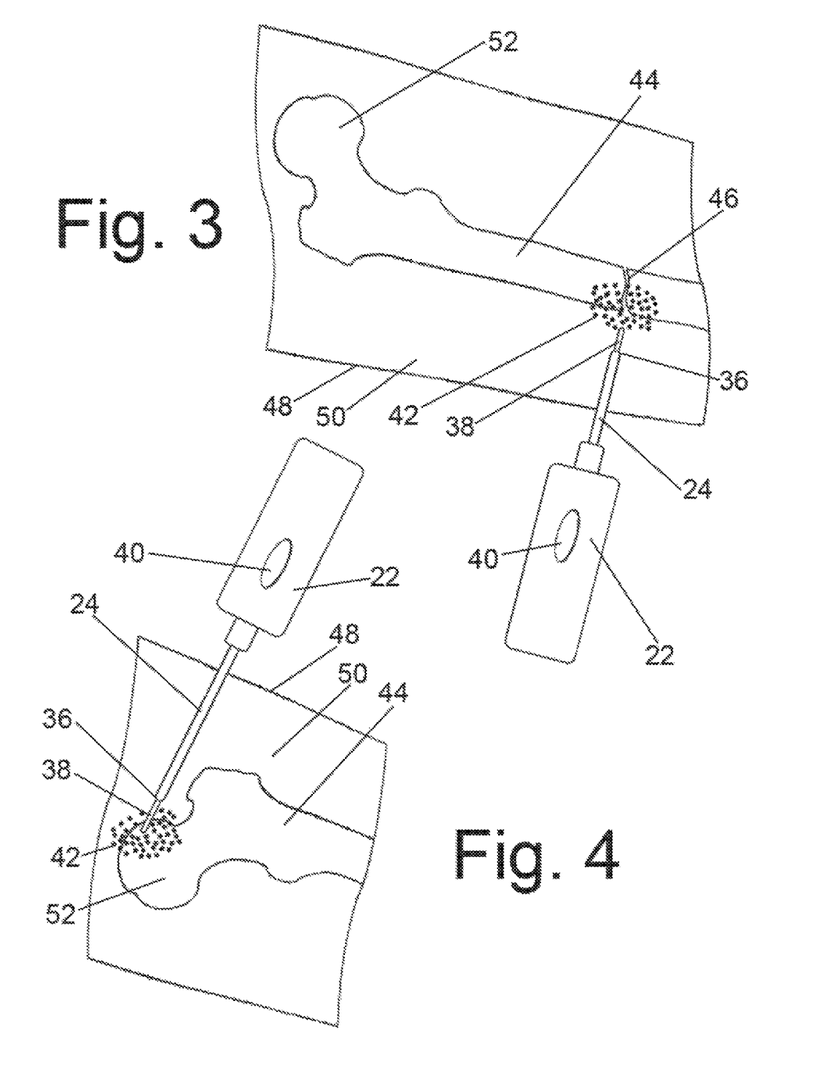
FIG. 3 is an illustration, partially in section, of the exemplary infra-red laser device of FIG. 1 shown in the process of treating a non-union or delayed union bone fracture in accordance with one exemplary method of this invention.
FIG. 4 is an illustration, partially in section, of the exemplary infra-red laser device of FIG. 1 in the process of treating avascular necrosis in accordance with another exemplary method of this invention.

FIG. 3 is an illustration of the exemplary infra-red laser device 20 of FIG. 1 shown in the process of treating a non-union or delayed union bone fracture by directing the IR laser beam 38 thereto in accordance with one exemplary method of this invention. In this example the femur 44 is fractured at 46. The skin of the patient's leg is designated by the reference number 48 and the thick thigh muscles are designated by the reference number 50. The needle 24 with its free end is introduced through the skin and intervening thigh muscles to a position closely adjacent the fracture 46. The laser device is then operated by the user pressing the ON/OFF button to the ON position, whereupon the IR laser beam is produced and exits the open free end of the needle to result in the distribution of the IR energy throughout the diffusion zone 42 so that it is at a maximum in the region of interest, e.g., the region along the bone portions contiguous with the fracture. This application of pulsed IF laser therapy for treatment of bone fracture with delayed union and non-union offers promising results by accelerating the healing process so it can be used as an important core therapy not only as an adjuvant therapy. The higher IR dose being provided by the device 20 stimulates MSCs, which should lead to new bone formation. Excess protein synthesis by DNA stimulation will synthesize much collagen protein which constitutes about 28% of bone mass. Moreover, the increased blood supply engendered by the IR radiation should accelerate the healing process because the immune system will clean the intervening soft tissue debris that may interfere with healing process. Lastly, the increased blood supply promotes local tissue oxygenation necessary for reconstruction of new bone.

FIG. 4 is an illustration of the exemplary infra-red laser device of FIG. 1 in the process of treating avascular necrosis (AVN) of the head 52 of the femur 44 by directing the IR laser beam 38 thereto in accordance with another exemplary method of this invention. To that end, the needle 24 with its free end is introduced through the skin and intervening thigh muscles to a position closely adjacent the situs of the AVN at the femur head 52. The laser device is then operated by the user pressing the ON/OFF button to the ON position, whereupon the IR laser beam is produced and exits the open free end of the needle to result in the distribution of the IR energy throughout the diffusion zone 42 so that it is at a maximum in the region of interest, e.g., the region encompassed by the AVN. Since AVN disease is characterized by ischemia (reduction of blood supply) of part of the bone leading to a devitalized tissue formation in the affected segment, the irradiation of the AVN region with the IR laser (which can reach the deep seated disease to stimulate and increase the blood supply thereat) should provide superior results than prior art IR laser techniques. Moreover, a larger amount of energy that the device and method of this invention is capable of providing should effect sufficient stimulation of MSCs to expedite the repair the ischaemic area with new bone formation. Furthermore, the increase blood supply plus the better tissue oxygenation via increased RBCs vitality act as accessory factors for accelerated healing of AVN. Lastly, the immune cells can invade the area and clean the devitalized tissues debris.

Figure 5:
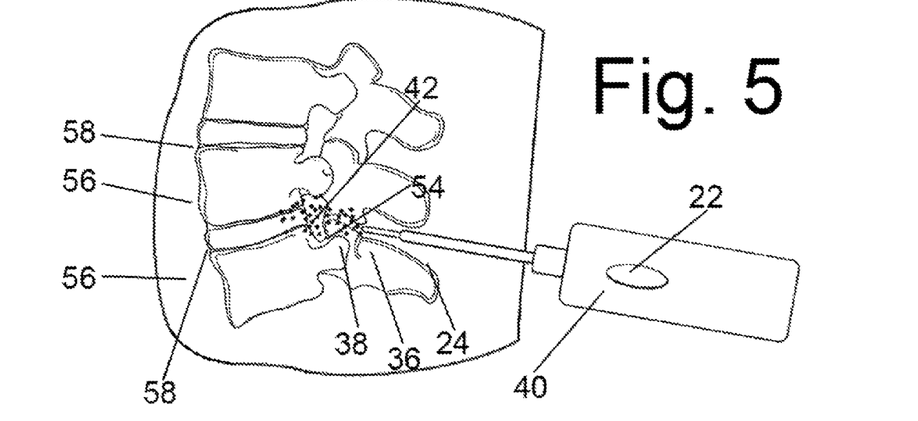
FIG. 5 is an illustration, partially in section, of the exemplary infra-red laser device of FIG. 1 in the process of treating chronic low back pain in accordance with another exemplary method of this invention.

FIG. 5 is an illustration of the exemplary infra-red laser device of FIG. 1 in the process of treating chronic low back pain by directing the infra-red laser beam to the facet joints, the back of the vertebral bodies and intervening discs of the spine in accordance with another exemplary method of this invention. Chronic low back pain is a group of diseases that affects a large number of the population (e.g., approximately 25 million in the United States), especially obese elderly women. While the results of the prior art treatment with an externally applied pulsed IR laser are generally good, they could clearly be better. The subject invention provides a greater chance of success in treating this group of diseases because the vertebral body and intervening intervertebral discs are approximately 3-4 inches or more from the skin. Therefore, as shown in FIG. 5 the needle 24 is introduced so that its free distal end 36 is located immediately adjacent a facet joint 54 and the back of vertebral bodies 56 and intervening discs 58, which are the sources of the back pain. At this time the laser device is operated to produce the IR laser beam 38, which is distributed throughout the diffusion zone 42 so that it is at a maximum in the region of interest, e.g., the facet joints, the back of the vertebral bodies and intervening discs of the spine.

A recent published paper asserts that the local heat by laser beam will increase the blood supply necessary for healing and removal of the mediators that are responsible for the pain and also the increased blood supply to the compressed nerves, which results in more nutrition to these compressed spinal nerves. Moreover, the immune cells clean the area of herniated discs which compress the spinal nerves. Thus, subsequently, the pain will subside. Furthermore, the IR laser increases the blood supply to the back muscles leading to their strengthening, which is essential part in protecting lumber discs. Recent studies show that MSCs around discs and the back of vertebrae can repair the damaged tissues and replace them with new tissues similar to the original ones. Thus the use of the laser device of this invention may provide benefits akin to that of a stem cell injection.

Figure 6:
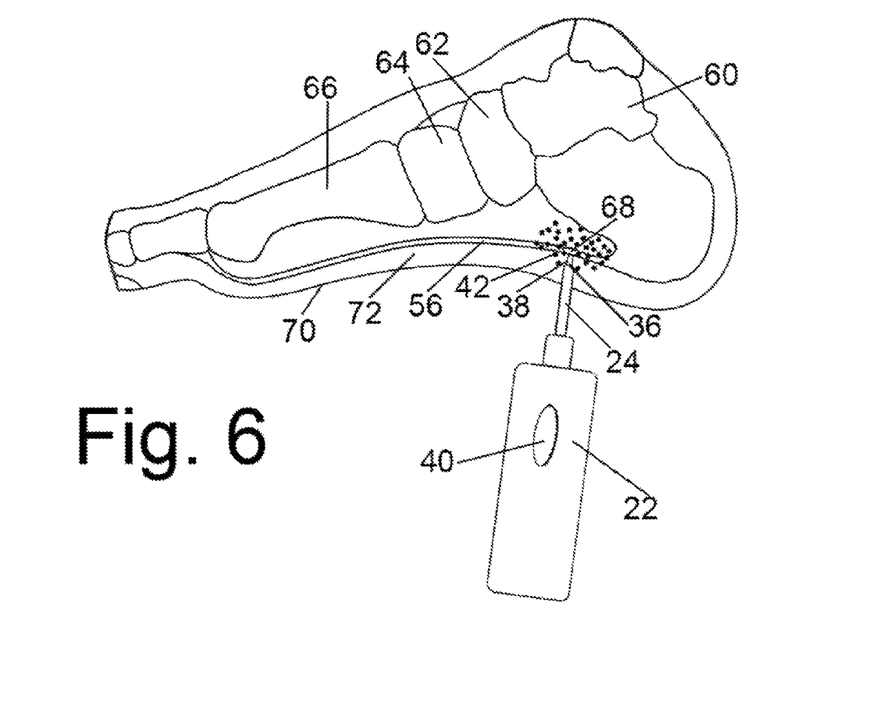
FIG. 6 is an illustration, partially in section, of the device shown in FIG. 1 in the process of treating plantar fasciitis in accordance with another exemplary method of this invention.

FIG. 6 is an illustration of the device shown in FIG. 1 in the process of treating plantar fasciitis in accordance with another exemplary method of this invention. In FIG. 6, the plantar fascia 56, which is a ligament that spreads from calcaneus 58 under the talus 60, the navicular 62, the cuneiform 64 and the metatarsals 66 to the toes, is shown with an exemplary tear 68 adjacent the calcaneus 58. Plantar fasciitis is the most common cause of heal pain and affects approximately 10 million persons in the United States. Repeated stretching of the plantar fascia, particularly by overweight persons, causes micro-tears therein. Such tears increase the inflammatory process as a compensatory mechanism to increase the blood supply, which is associated with painful mediators. As shown in FIG. 6, the laser device 20 is used to place the distal end 36 of the needle 24 immediately adjacent the tear 68 and the laser beam 38 activated to produce a diffusion zone 42 of IR energy that is at a maximum or concentrated at the tear. The application of IR energy to the situs of the tear should significantly increase local blood supply to the plantar fascia thereat, thereby improving recovery and healing. This action overcomes the disadvantages of the prior art externally applied pulsed IR lasers, because all of the IR laser energy is directed towards the exactly painful area (the area of micro-tears), without any loss of energy in the thick skin 70 of the sole and in the subcutaneous tissues 72, which would tend to absorb more than 70% of energy if the IR laser beam was externally applied like in the prior art.

Figure 7:
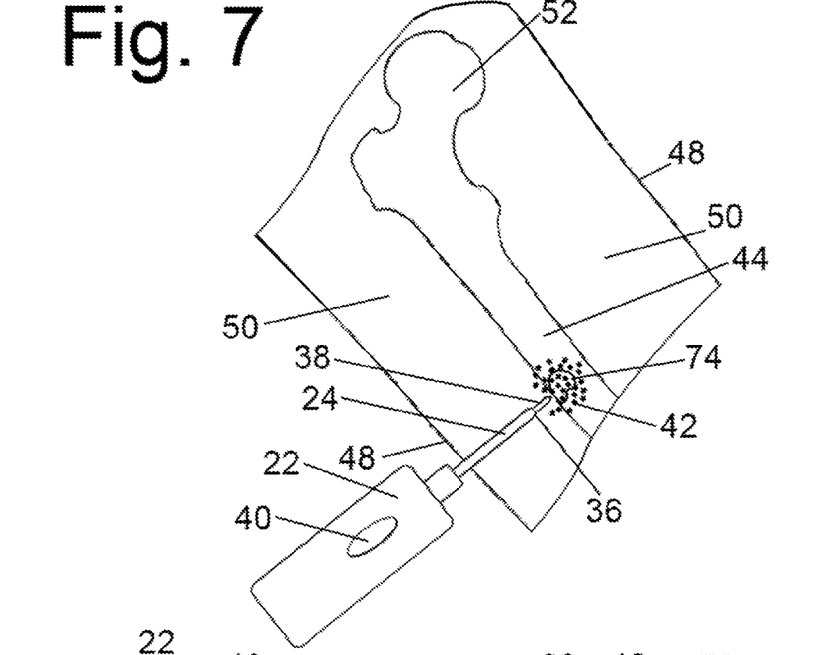
FIG. 7 is an illustration, partially in section, of the device shown in FIG. 1 in the process of treating Osteo-myelitis in accordance with another exemplary method of this invention.

FIG. 7 is an illustration of the device shown in FIG. 1 in the process of treating osteomyelitis in accordance with another exemplary method of this invention. Chronic osteomyelitis (septic bone infection) is catastrophic disease that is very difficult to treat and a full cure is sometimes impossible. It needs a long term course of treatment, sometimes over years with repeated surgical intervention in many cases. With this disease bacteria live in devitalized bone and hence are remote from the immune system. Many clinics claim that pulsed IR laser therapy improves the condition and reduces its course resulting from local heat production at the situs of the infection. This heat in turn increases the blood supply and raises the immunity by increasing the number of immune cells (macrophages and lymphocytes) in the affected devitalized bone. The skin barrier is very important in this condition because this disease needs the application of very high energy to the infection situs. The prior art devices for externally applying pulsed IR laser energy cannot deliver sufficient energy to the infection, which can be three or more inches below the skin surface, without risking damage to the skin of the patient. In contradistinction, the subject IR laser can be used to treat deep seated infections. For example, as shown in FIG. 6 the device 20 is shown in the process of treating a chronic osteomyelitis infection 74 within the femur 42 by introducing the free end 36 of the needle 24 to a position closely adjacent the situs 74 of the infection and operating it to produce a diffusion zone 42 of IR energy at a maximum or concentrated at the infection situs to heat that situs. Moreover, the high, focused, and very near IR laser is capable of stimulation of MSCs to enhance new bone formation (involucurum) to replace the devitalized one (sequestrum). Therefore, a pulsed IR laser constructed and used in accordance with this invention can be considered as an important core method of treatment not only as an adjuvant that can modify the course of treatment.

Figure 8:
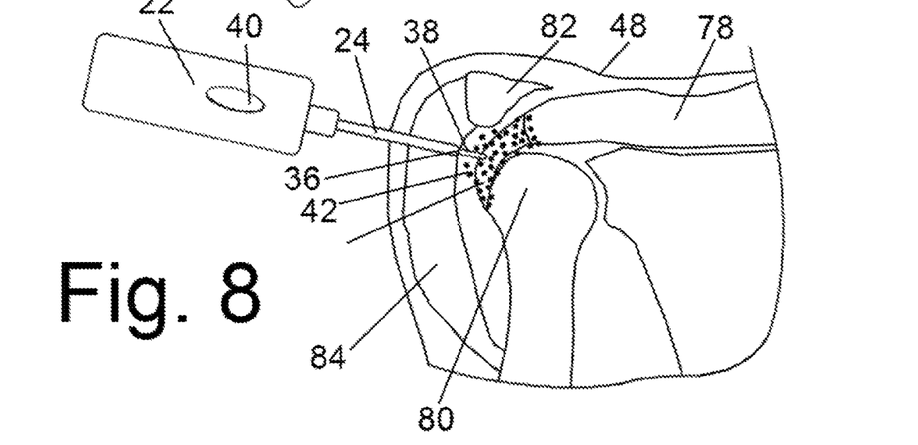
FIG. 8 is an illustration, partially in section, of the device shown in FIG. 1 in the process of treating supra-spinatus tendonitis in accordance with another exemplary method of this invention.

FIG. 8 is an illustration of the device shown in FIG. 1 in the process of treating supra-spinatus tendonitis in accordance with another exemplary method of this invention. Supra-spinatus tendinitis (also known as rotator cuff tear or impingement syndrome) is a condition that may start by ischemia of the supra-spinatus tendon and which will be presented as swelling of that tendon as a compensatory mechanism to enhance the blood supply. The problem is that the supra-spinatus tendon 76, which connects the supra-spinatus muscle 78 to the head of the humerus 80, is located inside a confined space between the head of humerus, the acromion bone 82 and the deltoid muscle 84. Thus, the swollen tendon will not be allowed to expand so that the pressure is increased, thereby aggravating the cycle of ischemia because of the high pressure compressing the blood vessels further. It has been determined that pulsed IR laser therapy improves the blood supply by the local heat, with absorption of excess fluids, so it reverses the whole disease process. Moreover, this local increase of blood supply helps in recovery of the tendon with removal of the mediators responsible for pain. To that end, as shown in FIG. 8 the IR laser device 20 of this invention can be used to treat this condition by introducing the free end 36 of the needle 24 through the thick deltoid muscle to a position closely adjacent the supra-spinatus tendon 76 and operating it to produce a diffusion zone 42 of IR energy at a maximum or concentrated thereat to heat the tendon. Thus, the laser device of the subject invention and its method of use is superior to the prior art because it transmits the IR laser energy directly near to supra-spinatus tendon without loss of any part of it in the skin, subcutaneous tissue or the very thick deltoid muscle. Because the subject invention can transmit a very large amount of IR laser energy very near to the tendon, it should stimulate MSCs that can repair some of the devitalized area of the tendon and replace them with new tendon substance. Moreover, the IR laser energy should assist in the unwinding of double helix DNA to stimulate new collagen protein synthesis which constitutes 50% of the substance of the tendon materials.

Figures 9, 10:
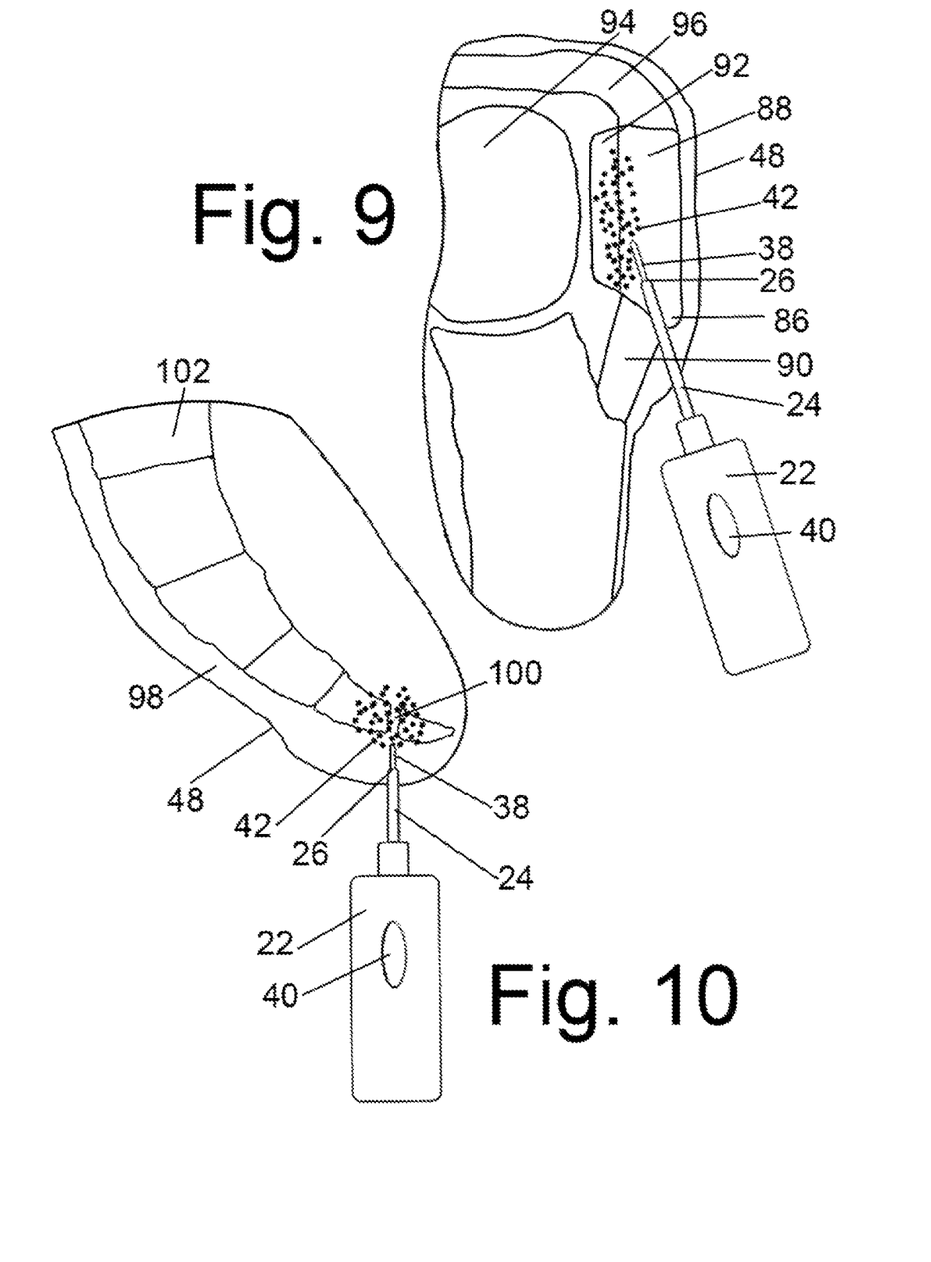
FIG. 9 is an illustration, partially in section, of the device shown in FIG. 1 in the process of treating patello-femoral maltracking in accordance with another exemplary method of this invention.
FIG. 10 is an illustration, partially in section, of the device shown in FIG. 1 in the process of treating Coccydynia in accordance with another exemplary method of this invention.

FIG. 9 is an illustration of the device shown in FIG. 1 in the process of treating patello-femoral maltracking in accordance with another exemplary method of this invention. Patellofemoral maltracking is the most common cause of anterior knee pain. There is a new theory of this particular disease process that is a result of extensive studies in the United States. The new theory is called "tissue homeostasis theory" and claims that the starting point is ischemia of the lateral retinaculum of the patella which contracts with subsequent neural tissue infiltration in the lateral retinaculum. The contracted lateral retinaculum pulls the patella laterally resulting in lateral tilt of the patella with subsequent damage of patellar cartilage by high friction of the patellar cartilage with uneven maltrack. The damaged patellar cartilage causes severe pain with each flexion-extension of the knee. Prior art pulsed IR laser therapy can improve the condition by its application to anterior part of knee, which will increase the blood supply to the ischemic area and washing the pain mediators. However, such action is not effective in regeneration of damaged patellar cartilage which is the main source of pain. As shown in FIG. 9, the laser device 20 of this invention can be used to treat this condition by introducing the free end 36 of the needle 24 through the skin 48 and the lower pole 86 of the patellar bone 88 (and possibly the patellar tendon 90) to the articular cartilage 92. The articular cartilage 92 is interposed between patellar bone 88 and the femur condyle 94 adjacent the quadriceps muscle 96. Since the needle will have to pass through the lower pole of the patella (hard bone as opposed to soft tissue), anesthesia will likely be required. The IR laser device 20 can then be activated to produce the laser beam 38 to produce a diffusion zone 42 of IR energy at a maximum or concentrated at the articular cartilage, which is very difficult to be reached by the prior art because of skin, subcutaneous tissues, and patellar bone barriers. The IR laser produced by the subject invention and directed to the region of interest helps in regeneration of the patellar cartilage by stimulating chondrocytes to repair the damaged cartilage. IR laser also stimulates the MSCs in cartilage stoma to produce more chondrocytes to synthesize more new cartilage. This technique is exemplary in repairing the actual cause of pain, which is the damaged patellar cartilage plus the initiating factor of lateral retinacular ischaemia because the diffusion zone of radiation reaches these sites by good concentration without barriers.

FIG. 10 is an illustration of the laser device 20 of FIG. 1 shown in the process of treating coccydynia in accordance with another exemplary method of this invention. Coccydynia is pain at lowest part of the spinal column. It is of unknown cause, but most probably it is due to injury of sacrococcygeal ligament. It is more common in women after giving birth and occurs to lesser extent in males. It is difficult and refractory to treat and there is a great deal of individual variations in response to treatment. Sometimes, even surgical excision may not be helpful.

Many clinics in the United States and Canada have claimed that pulsed IR laser therapy has an excellent response, especially in cases which have poorly responded to other medical treatments. However, getting the IR laser to a deep seated situs where this condition typically resides can be problematic. The IR laser device of this invention offers a significant modality for treating coccydynia irrespective of the depth of the sacro-coccygeal joint from the skin. To that end, as can be seen in FIG. 10 the laser device 20 is used by introducing the free end 36 of the needle 24 through the skin 48 and the subcutaneous tissue (thick fat) 98 to a position closely adjacent the sacro-coccygeal joint 100 of the sacrum 102. The IR laser device can then be activated to produce the laser beam 38 to produce a diffusion zone 42 of IR energy at a maximum or concentrated at the sacro-coccygeal joint 100 to heat it. As with the other methods described above, the subject invention concentrates IR laser energy at the painful sites so there would be a higher incidence of improvement than with a conventional externally applied pulsed IR laser. The increase blood supply helps rapid healing of damaged tissue and washing out the mediators that are responsible for pain. The increased blood supply also enhances more immune cells to invade the zone of diffusion clearing all tissue debris that delay healing.

Figures 11A, 11B:
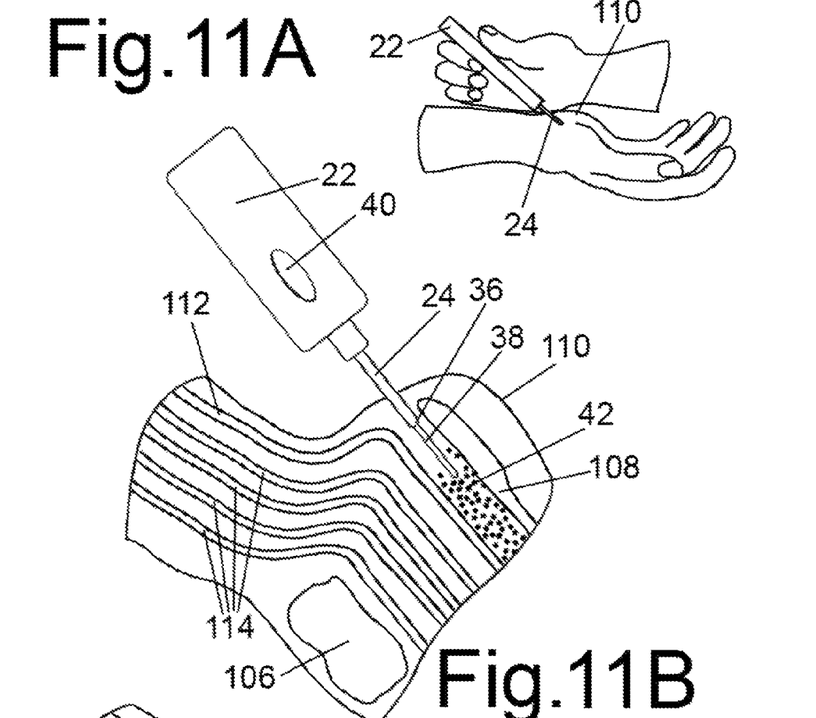
FIG. 11A is a reduced size illustration of the device shown in FIG. 1 in the process of treating carpal tunnel syndrome in accordance with another exemplary method of this invention.
FIG. 11B is a larger size illustration, partially in section, of the device shown in FIG. 11A in the process of treating carpal tunnel syndrome in accordance with another exemplary method of this invention.

FIG. 11 is an illustration of the device shown in FIG. 1 in the process of treating carpal tunnel syndrome in accordance with another exemplary method of this invention. Carpal tunnel syndrome is a disease characterized by oedema fluid collection and swelling in the soft tissue of the flexor compartment of the hand in front of the carpus bone 106. The transverse carpal ligament 108, which is located on the palmar side 110 of the hand will be tightened by oedema fluid and subsequently will compress the median nerve 112 (which is located adjacent the flexor tendons 114). Pulsed IR laser treatment helps to increase the blood supply, which will lead to absorption of oedema fluid. The prior art is less efficient because the diffusion zone of IR is mostly absorbed by skin, subcutaneous tissues and thick transverse carpal ligament. Very minimal IR laser energy can cross all these barriers. To that end, as can be seen in FIG. 11 the laser device 20 is used by introducing the free end 36 of the needle 24 through the skin 48 and the subcutaneous tissue to a position just under the transverse carpal ligament 108 and above the median nerve 112. The IR laser device can then be activated to produce the laser beam 38 to produce a diffusion zone or region 42 of IR energy at a maximum or concentrated at that region to heat it. As with the other methods described above, the subject invention concentrates IR laser energy at the painful sites so there would be a higher incidence of improvement than with a conventional externally applied pulsed IR laser. The increase blood supply helps rapid healing of damaged tissues and removes the mediators that are responsible for pain plus absorption of oedema fluids leading to pain subsidence. In addition, recent studies show that laser therapy increases formation of elastic fibers from nearby MSCs. This will cause the transverse carpal ligament to become more elastic and relaxes with much improvement of the condition of carpal tunnel.

Figure 12:
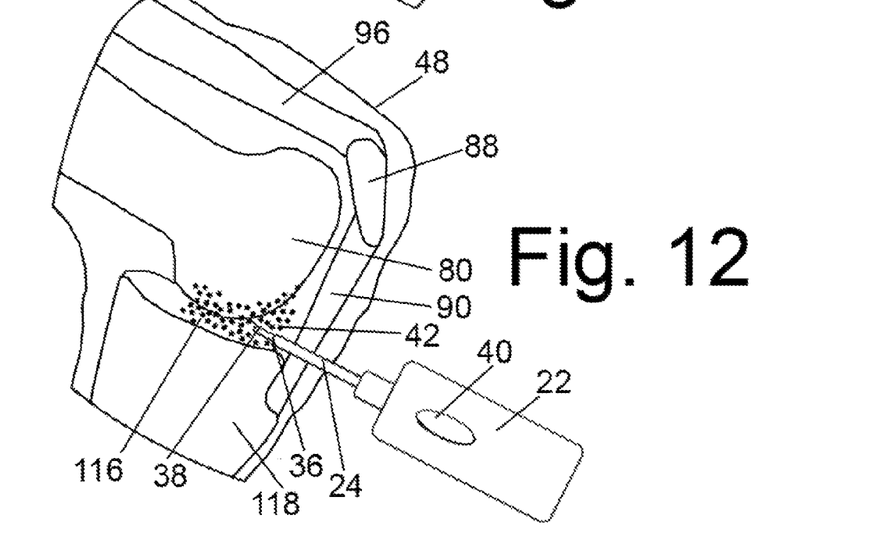
FIG. 12 is an illustration, partially in section, of the device shown in FIG. 1 in the process of treating Osteo-arthritic joint disease in accordance with another exemplary method of this invention.

FIG. 12 is an illustration of the device shown in FIG. 1 in the process of treating osteo-arthritic joint disease (e.g., the tibia-femur joint of the knee) in accordance with another exemplary method of this invention. Osteo-arthritic joint diseases are degenerative joint diseases which break down the articular cartilage which become thin, eroded, and sometimes ulcerated with reduction lubricant materials (e.g., synovial fluids) leading to painful movements. Pain of mild to moderate arthritis can be improved by prior art pulsed IR laser therapy. The mechanism of action is by local increase of the blood supply to the joint and surrounding muscles. The increase of local blood supply should lead to stimulation of the lubricant materials. It should also stimulate healing of the ulcers and facilitate washing of the mediators that are responsible for pain. Moreover, IR enhances the immune cells to clear all tissue debris that are always associated with osteo-arthritis. This can be applied to any joint, but clinically this method is used in the hip and knee joints. The IR laser devices of the subject invention provide a more viable means for achieving that end. In particular, as shown in FIG. 12 the laser device 20 is used by introducing the free end 36 of the needle 24 through the skin 48, through the subcutaneous tissue and through the patellar tendon 90 to the articular cartilage 116 between the femur 80 and the tibia 118. The IR laser device can then be activated to produce the laser beam 38 to produce a diffusion zone or region 42 of IR energy at a maximum or concentrated at the articular cartilage 116 to heat it and produces all the above benefits much more than that of the prior art because of the higher dose of IR.

Figure 13:
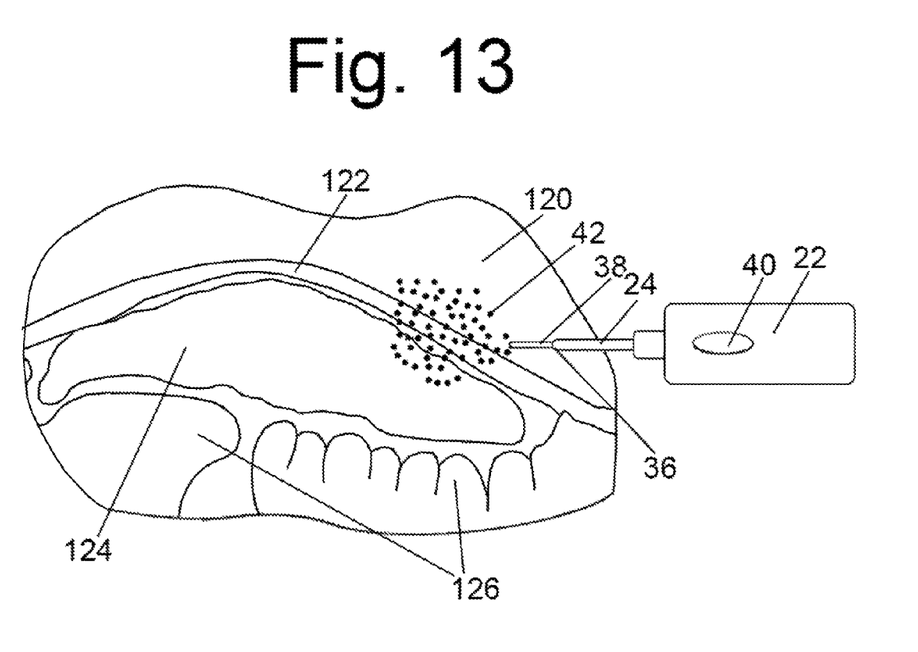
FIG. 13 is an illustration, partially in section, of the device shown in FIG. 1 in the process of reducing fat in accordance with another exemplary method of this invention.

FIG. 13 is an illustration of the device shown in FIG. 1 in the process of reducing abdominal fat and visceral fat in accordance with another exemplary method of this invention. While this methodology is not purely orthopedic in nature, it still constitutes part of this invention for two main reasons. First, a reduction of abdominal fat will greatly reduce the mechanical stresses on the joints of the lumbar spine, the pelvis, and the lower limbs. In other words, the reduction of abdominal fat helps to protect the joints of spine, pelvis and lower limbs. The second reason is considered as a prophylactic measure to prevent orthopedic problems before their occurrence. In this regard, the method of FIG. 13 is a preventive one to avoid orthopedic diseases, particularly since a significant number of orthopedic diseases occur in old and debilitated persons. Thus, with the subject invention the IR laser when used on abdominal fat serves to activate the deep seated stem cells and repair damaged tissues, including the orthopedic system, e.g., repairing joint cartilage which tends to prevent or delay the progress of osteo-arthritis, repair ischaemic tendon to avoid tear, stimulation of bone cells to synthesize new bone formation to avoid fracture and so on.

To accomplish the reduction of abdominal fat the free end 36 of the needle 24 of the IR laser device 20 is inserted through the skin through the subcutaneous tissue and into the abdominal fat 118 at any desired position therein. The IR laser device can then be activated to produce the laser beam 38 to produce a diffusion zone or region 42 of IR energy at a maximum or concentrated within that fat to heat it and thereby activate its stem cells. The diffusion zone can cross the thin and stretched abdominal muscles 122 to reach the underlying deeper visceral fat 124 overlying the abdominal viscera 126, a function unavailable through the use of prior art externally applied IR lasers.

As should be appreciated by those skilled in the art from the foregoing the subject invention offers numerous advantages over the conventional pulsed IR laser therapy. In particular, the subject invention by-passes the skin barrier and allows penetration to deeper tissues/structures, e.g., three inches or greater. In fact devices constructed in accordance with this invention and their methods of use can apply IR energy at any depth within the body of the patient by the selection of an appropriate sized needle. Since the skin and underlying tissue is by-passed, an IR laser, e.g., a pulsed IR laser, constructed in accordance with this invention can apply maximum energy to the region of interest without fear of skin damage. Moreover, the IR beam can be precisely directed to the region of interest by merely orienting the needle in the desired direction and to the desired depth, thereby by-passing all unnecessary tissue barriers.

The devices and methods can be used to treat internal structures, e.g., nerves, muscles, blood vessels, cartilage and bone, with IR laser beams in the range of 200 mW to 500 mW, with the dosage being adjustable and based on conditions and the application desired. For example, in the case of osteomyelitis, the laser can be 500 mW. Moreover, the IR laser source can be arranged to produce a near infra-red laser beam in the range of approximately 0.7 µm to 3.0 µm or a far infra-red laser beam in the range of approximately 50 µm to 1000 µm, again according to conditions and the application desired.

Without further elaboration the foregoing will so fully illustrate our invention that others may, by applying current or future knowledge, adopt the same for use under various conditions of service.

We claim:

1. A method of treating an orthopedic disease or condition of a patient by the irradiation of an orthopedic region of interest located within the body of the patient, said method comprising:

a) providing a device comprising a housing and a needle, said needle being an elongated member having a proximal end, a sharpened distal end and a hollow passageway extending therethrough from said proximal end to said distal end, said housing comprising an infra-red laser source located therein arranged when activated to produce a collimated infra-red laser beam to enter into said hollow passageway at said proximal end of said needle and pass therethrough to exit said distal end of said needle;

b) introducing said needle into the body of the patient by causing said sharpened distal end to pierce the skin and underlying tissue so that said distal end of said needle is located at the orthopedic region of interest; and c) activating said laser source to produce a far infra-red laser beam in the range of 50 µm to 1000 µm, said infra-red laser beam being in the range of 200-500 milliwatts of energy, whereupon said infrared laser beam exits said distal end of said needle to impinge said orthopedic region of interest without the intervening skin and underlying tissue attenuating said infra-red laser beam.

2. The method of claim 1 wherein said the laser source is either a continuous infra-red laser beam or a pulsed infra-red laser beam.

3. The method of claim 1 wherein said disease or condition is Coccydynia.

* * * * *